United States Patent [19]

Clairmont et al.

[11] Patent Number: 4,688,794
[45] Date of Patent: Aug. 25, 1987

[54] MEDICAL EXERCISE APPARATUS

[76] Inventors: Gregory P. Clairmont; Sheila E. Woodward, both of R.D. #1, Box 20, Huntington, Vt. 05462

[21] Appl. No.: 865,456

[22] Filed: May 21, 1986

[51] Int. Cl.⁴ .......................... A63B 1/00; A61F 5/00
[52] U.S. Cl. ......................................... 272/93; 128/79
[58] Field of Search ......... 272/93, 125, 137, DIG. 10; 433/140; 128/341, 79, 361, 31

[56] References Cited

U.S. PATENT DOCUMENTS

| 988,120 | 3/1911 | Lott | 128/341 |
|---|---|---|---|
| 3,312,222 | 4/1967 | Dwyer | 128/361 |
| 3,502,328 | 3/1970 | Hamilton | 128/79 |
| 3,712,300 | 1/1973 | Davidowitz | 128/341 |
| 4,240,412 | 12/1980 | James | 128/341 |
| 4,241,912 | 12/1980 | Mercer et al. | 128/79 |
| 4,574,791 | 3/1986 | Mitchener | 128/79 |

FOREIGN PATENT DOCUMENTS

| 0536196 | 5/1941 | United Kingdom | 128/360 |
|---|---|---|---|
| 2058571 | 4/1981 | United Kingdom | 128/79 |

Primary Examiner—Richard J. Apley
Assistant Examiner—S. R. Crow
Attorney, Agent, or Firm—Thomas N. Neiman

[57] ABSTRACT

This invention is for an apparatus which is used to stretch the perineum of a pregnant woman through a self exercise program. The apparatus consists of an arcuate curved handle made of a sturdy, durable material. The handle is designed to allow the user to grasp each of the opposite ends of the handle with each hand. At the centerpoint of the outside edge of the handle, an extension shaft extends outwardly away from the handle. The shaft is capped off with an offset "Y" shaped saddle which is made of the same durable material as the handle but it is covered with a softer, resilient and easily cleaned material.

1 Claim, 5 Drawing Figures

MEDICAL EXERCISE APPARATUS

This invention pertains to means for physical exercise of the body and, in particular, to such means for an apparatus designed to stretch the perineum of a pregnant woman in order to minimize the necessity of a surgical incision (an episiotomy) of the vulvar oriface to aid in the delivery of the newborn.

The perineum is the anatomical region at the lower end of the trunk between the thighs. On the surface of the body it is limited in the front by the mons vereris in the female, behind by the buttocks and laterally by the medial sides of the thighs. Internally, it is bounded by the pubic arch and the arcuate ligament, behind by the tip of the coccyx, and at the sides by the ischiopubic rami and the saccrotuberous ligaments.

It is the current practice for trainers in pre-natal courses to teach the art of self physical exercise to the pregnant woman during the third trimester. This consists of a series of pressing and releasing actions by the pregant woman, inserting her thumbs into the vagina so as to stretch the perineal region more elastic. However, this method of self physical exercise, as is recommended, becomes nearly impossible for the pregnant woman to perform because of the inaccessibility to reach this defined area. Physical exercise devices, as shown by way of example, such as the U.S. Pat. issued to C. H. Spooner, No. 2,806,699 on Sept. 17, 1957 for an Exercising Device and the British Pat. No. 952,026 on Mar. 11, 1964 to Dirk Schmidt-Dincklage for a Gymnastic Exercising Device have similiarities. Both of those devices are twin gripped handles with spring tensioning means to provide user with a resistance to enhance physical conditioning. However, these devices do not have the proper design, when compared to the disclosed invention, to permit suitable exercise of the perineal region.

It is the object of this invention to set forth an apparatus to aid in the physical exercise of the perineum. It is also the object of this invention to teach an apparatus that provides useful, comfortable and safe exercise for the perineal region. Further, it is the object of this invention to teach a simple apparatus that can easily be cleaned and maintained. Another object of this invention is to teach a method of using this apparatus.

Especially, it is the object of this invention to teach a medical exercise apparatus, for safe and effective stretching of the perineum, comprising a shaft; means attached to said shaft to permit for the comfortable contact with the body; handles for manipulation of said apparatus; and said handles form an arcuate curved structure. Further objects of this invention, as well as the several features thereof, will become more apparent by reference to the following description taken in conjunction with the accompanying figure, in which.

Figure 1:
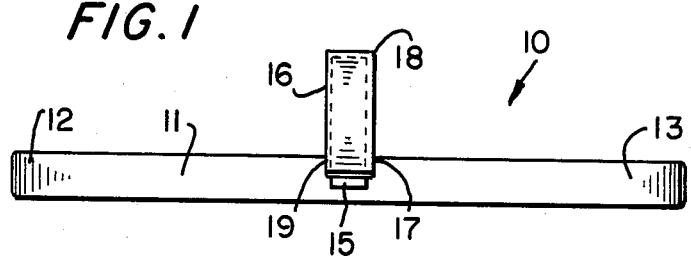
FIG. 1 is a top view of the novel medical exercise apparatus.
Figure 2:
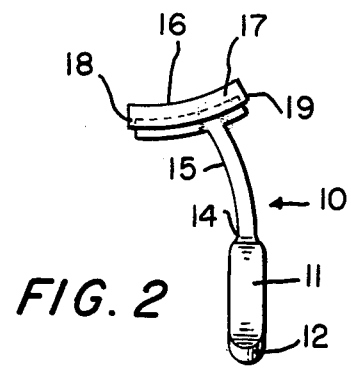
FIG. 2 is a side view thereof.
Figure 3:
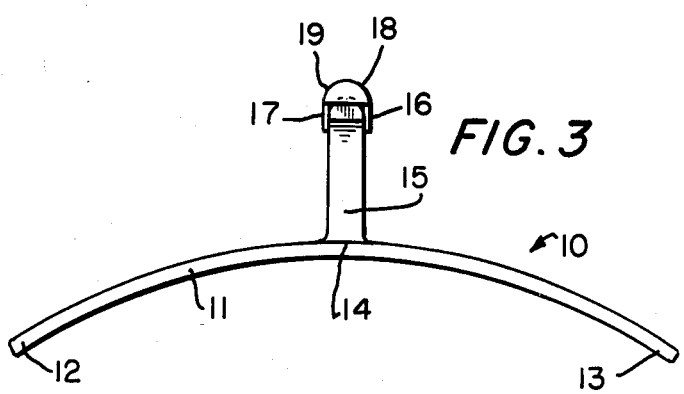
FIG. 3 is a frontal view thereof.
Figure 4:
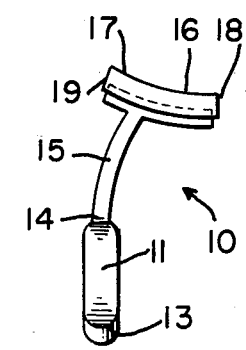
FIG. 4 is an opposite side view of the apparatus as compared with the view shown in FIG. 2.
Figure 5:
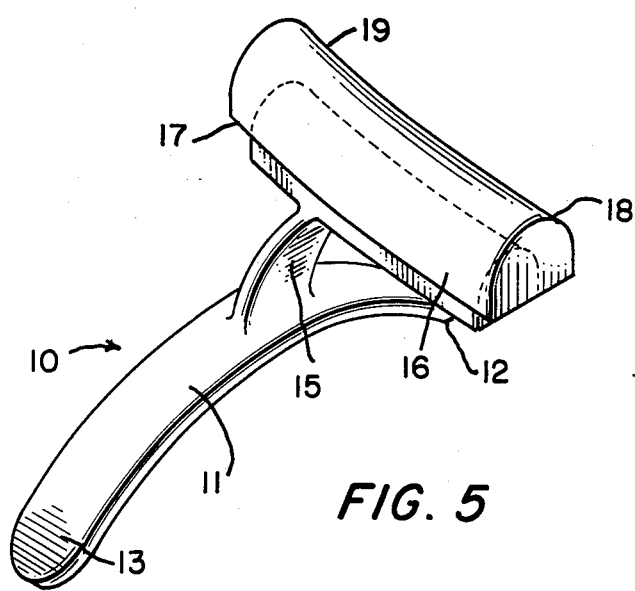
FIG. 5 is a perspective view of the novel apparatus.

The object and overall goal of the apparatus are shown in the figures. The medical exercise apparatus 10 comprises an arcuate curved semi-circle handle 11 which is gripped on ends 12 and 13 by the individual exercising. The handle measures an arc of at least one-sixth of a circle, but not more than one-third of a circle. At the centerpoint 14 of the handle 11 extends an extension shaft 15 which projects outward away from the ends 12 and 13 of the handle 11. The extension shaft 15 is topped off with a Y-shaped fixture 16 formed thereon, the fixture 16 being defined by a short section 17 and a long section 18 converging at the extension shaft 15. The inner surface of the fixture forms a concave shape. The entire apparatus 10 is made of a durable, sturdy material such as metal or plastic which is lightweight and easy to clean. The Y-shaped saddle 16 is covered with a soft, resilient material 19 designed to provide safety and comfort to the exerciser.

In practice, the user would grasp the novel apparatus 10 at the ends 12 and 13. The ends 12 and 13 would be held away from the user. The longer section 18 of the saddle 16, at the edge of the extension shaft 15, is especially to be inserted into the vagina. The shorter section 17 exerts pressure on the external portion of the perineum. Pressure is exerted as the exerciser pushes the ends 12 and 13 of the handle 11 in a downward motion, and then releases. These repeated actions eventually provide more elasticy to the perineal region which will, in turn, minimize the necessity of requiring an episiotomy to be performed when the child is being delivered.

Accordingly, while we have described our apparatus in connection with a specific embodiement thereof, it is clearly to be understood that this is done only by way of example and not as a limitation to the scope of our invention as set forth in the objects therof and in the claims.

We claim:

1. A medical exercise apparatus, for safe and effective stretching of the perineum, comprising:

a shaft;

means attached to said shaft to permit for the comfortable contact with a user's body;

handles for the manipulation of said apparatus;

said handles comprise an arcuate curved structure measuring an arc of at least one-sixth of a circle, but not more than one-third of said circle;

said shaft extends outwardly from the centerpoint of said handle and away from the ends of said handle;

said attached means includes engaging means;

said engaging means comprises an unequal elongated Y-shaped fixture formed by a pair of different sized sidewalls which extend outwardly and away from the shaft;

said sidewalls converge at said shaft;

the angle of the inner surface of said sidewall is concave;

the longer of said sidewalls is designed for providing pressure on the inner surface of perineum;

the shorter of said sidewalls is designed for providing pressure on the outer surface of the perineum; and said Y-shaped fixture has resilient covering means.

* * * * *